United States Patent

Shirazi et al.

[11] Patent Number: 5,827,420
[45] Date of Patent: Oct. 27, 1998

[54] METHOD AND APPARATUS FOR THE GENERATION OF NITRIC OXIDE

[75] Inventors: Shahram Z. Shirazi; Valentin Zhelyaskov, both of Sarasota, Fla.

[73] Assignee: World Precision Instruments, Inc., Sarasota, Fla.

[21] Appl. No.: 902,568

[22] Filed: Jul. 29, 1997

[51] Int. Cl.[6] .............................. C25D 5/48; C25D 3/38; C25B 1/00; C25B 1/22

[52] U.S. Cl. ........................ 205/220; 205/291; 205/464; 205/553

[58] Field of Search ................................. 205/220, 291, 205/464, 491, 551, 553

[56] References Cited

U.S. PATENT DOCUMENTS

| 4,287,040 | 9/1981 | Alamaro | 204/179 |
| 4,427,504 | 1/1984 | Stucki | 204/101 |
| 5,396,882 | 3/1995 | Zapol | 128/200.14 |

*Primary Examiner*—Kathryn L. Gorgos
*Assistant Examiner*—Edna Wong
*Attorney, Agent, or Firm*—Alix, Yale & Ristas, LLP

[57] ABSTRACT

A gas mixture having a preselected concentration of nitric oxide, usable in inhalation therapy for example, is produced by controllably establishing the coulometric reduction of copper ions in a solution of nitric acid accompanied by purging the chamber in which the reduction reaction occurs with an inert gas. A free-standing, portable NO generator for use in the production of such a gas mixture is also disclosed.

10 Claims, 4 Drawing Sheets

5,827,420

METHOD AND APPARATUS FOR THE GENERATION OF NITRIC OXIDE

BACKGROUND OF THE INVENTION

1. Field of the Invention

The present invention relates to the generation of nitric oxide gas and, particularly, to an electrochemical process which permits precise control over the rate of production of nitric oxide. More specifically, this invention is directed to a precision nitric oxide gas generator and, especially, to a free-standing, portable coulometric generator of controllable amounts of high purity nitric oxide. Accordingly, the general objects of the present invention are to provide novel and improved methods and apparatus of such character.

2. Description of the Prior Art

Nitric oxide (NO) has been shown to play a significant role in the regulation of many biochemical pathways in organisms. See to "Nitric oxide: Physiology, Pathophysiology, and Pharmacology", M. Moncada, Pharmacological Review, vol. 30, pages 109–142, 1990 and "Biosynthesis and Methabolism of Endothelium-derived Nitric Oxide:, L. J. Ignarro, Annu. Rev. Pharmacol. Toxicol., vol. 30, pages 535–560, 1990. Nitric oxide has been proven to be an important modulator of vascular, cardiovascular, nervous and immune systems as well as other homeostatic mechanisms. Reference is also made to "Inhaled Nitric Oxide: A selective pulmonary vasodilator reversing human hypoxic K pulmonary vasoconstriction (HPV)", Z. Blomquist, Circulation, vol. 84, No. 4, page 361, 1991 and "Involvement of nitric acid in the reflex relaxation of the stomach to accommodate food or fluid", K. M. Desai et al, Nature, vol. 351, No. 6, page 477, 1991 for discussions of the therapeutic effects of NO.

The usage of inhaled NO gas as a selective therapeutic agent for the treatment of pulmonary and cardiovascular ailments is also reported in "Inhaled nitric oxide as a cause of selective pulmonary vasoldilation in pulmonary hypertension", J. Perke-Zaba et al, The Lancet, vol. 338, No. 9, page 1173, 1991. It has recently been established that the administration of 5 to 80 ppm of NO in respiratory gases drastically improves persistent pulmonary hypertension of newborn children within a few minutes. This important medical application of NO gas is discussed in "Inhaled nitric oxide in persistent pulmonary hypertension of the newborn" by J. D. Roberts et al, The Lancet, vol. 340, 1992.

The administration of NO gas at low concentration for the treatment of the aforementioned disorders has not to date revealed any unfavorable side effects. The lack of adverse side effects may be attributable to the fact that the therapeutic properties of NO specifically target the organ subjected to the treatment. The selectivity in such treatments is mediated by the intrinsic properties of NO which allows its relatively rapid oxidation by hemoglobin. A further advantage in using NO therapy is the quick onset of action, usually within minutes, when compared to a delay of up to 90 minutes as experienced in the case of alternate available drug therapy. See U.S. Pat. No. 5,396,882 to Zapol.

Conventional treatment of pulmonary and cardiovascular abnormalities has, in spite of the abovediscussed benefits incident to using NO, to date primarily involved the use of beta antagonists and anticholinergic drugs. Such drugs have adverse side effects including allergic anaphylactic reactions, cardiac arrhythmic, anorexia, nausea, vomiting, anxiety and headaches. These adverse side effects are discussed in above-reference U.S. Pat. No. 5,396,882.

The failure of NO therapy to achieve widespread usage is primarily attributable to the previous lack of a precision NO gas generator suitable for clinical and biomedical applications. Thus, medical use of NO has required the availability of tanks of commercially manufactured gas which are diluted and mixed with carrier gases for administration. The storage, transport and use of such commercially manufactured gas is difficult and inconvenient.

Historically, NO gas has been commercially manufactured using the well-known Ostwald process in which ammonia is catalytically converted to NO and nitrous oxide at a temperature above 800° C. The Ostwald process is discussed in U.S. Pat. No. 4,272,336; 4,774,069 and 5,478,549. The Ostwald process, while suitable for the mass production of NO at high temperatures in an industrial setting, is clearly not applicable to clinical or home use. Other methods of NO gas generation are based on Haber-Bosch synthesis, as described in U.S. Pat. No. 4,427,504, or by taking advantage of paramagnetic properties of nitrous oxide, as described in U.S. Pat. No. 4,139,595. Neither of these techniques is suitable for clinical or home use and significant industrial application thereof has not been reported. Yet another method for the generation of NO, which has found limited use in analytical laboratories, relies upon the reaction of 8 molar nitric acid with elemental copper.

This method is described by F. A. Cotton in the text "Advanced Inorganic Chemistry", 5th edition, pages 321–323, John Wiley & Sons, New York, 1988.

There have been recent attempts to devise apparatus for accurately delivering variable concentrations of NO.

By way of example, U.S. Pat. No. 5,396,882 describes a proposal for the generation of NO in an electric discharge in air. In the implementation of this proposed technique, electrodes would be separated by an air gap in an arc chamber. The establishment of a high voltage across the air gap would produce a localized plasma for breaking down oxygen and nitrogen molecules and thereby generate a mixture of NO, ozone and other $NO_x$ species. In theory, the concentration of NO could be varied by adjusting the operating current. The gas mixture produced by the process would be purified and mixed with air in order to obtain therapeutically significant concentrations of NO for administration to a patient. The process proposed in U.S. Pat. No. 5,396,882 would, however, inherently be susceptible to fluctuations in internal and external operating parameters, particularly the ambient humidity. Since the therapeutically useful range of NO concentration is relatively small, it is imperative that the concentration of administered NO be precisely controlled. In the process of U.S. Pat. No. 5,396,882, for example, the achievement of such control would dictate that the NO concentration be closely monitored at all times. Since the weight of NO generated by the process of U.S. Pat. No. 5,396,882 will vary with fluctuations in operating parameters, the monitoring of NO concentration would, at best, be extremely difficult and expensive to achieve. Indeed, a chemiluminescence analyzer would have to be incorporated into the apparatus and the size and cost of such an analyzer would adversely affect the cost and portability of the apparatus.

SUMMARY OF THE INVENTION

The present invention overcomes the above-discussed and other deficiencies and disadvantages of the prior art and, in so doing, provides a novel method by which NO can be safely and quantitatively generated. The method of the present invention is based upon the production of NO through the coulometric reduction of copper (II) ions ($Cu^{+2}$)

in a solution of nitric acid accompanied by purging the reaction chamber with an inert gas such as nitrogen. The invention also encompasses a new and improved apparatus for producing NO which implements this novel process and, in so doing, provides a free-standing, portable NO generator capable of precise control.

In the practice of the present invention, metallic copper is added to very concentrated nitric acid to generate NO gas at a rate dependent on the amount, i.e., the weight, of the added copper. The metallic copper is added quantitatively and reproducibly by electroplating pure, i.e., elemental, copper from a solution comprising copper sulphate and nitric acid onto an electrode. The thus deposited elemental copper is immediately consumed by the acid, thereby generating NO and converting the metallic copper to copper ions. The rate at which copper metal is created and used is a direct function of the quantity of electric charge, i.e., the current, consumed in the electroplating process. The efficiency of conversion of electrode charge to copper is nearly 100%. For every six electrons of charge transferred, three copper cations are reduced, and in turn, two molecular NO gas are produced. The electric current supplied to the reaction is easily measured and is a function of the amount of NO gas generated. The chamber where the reaction occurs is flushed with the inert carrier gas, at a constant flow rate, and the resultant gas mixture is washed in a buffer solution, so as to remove traces of nitric acid vapor that might be present in the gas phase, prior to administration.

BRIEF DESCRIPTION OF THE DRAWINGS

The present invention may be better understood, and its numerous objects and advantages will become apparent to those skilled in the art, by reference to the accompanying drawing wherein like reference numerals refer to like elements in the several Figures and in which.

DESCRIPTION OF THE DISCLOSED EMBODIMENT

The present invention relies on the reaction of nitric acid with elemental copper and proceeds instantaneously to produce nitric oxide and copper (II) ions in accordance with the following stoichiometric reaction:

(1) 

The elemental copper employed in the reaction of equation (1) is itself produced by a coulometric reduction of $Cu_{+2}$ in a mixture of nitric acid and copper (II) sulphate. This reaction is as follows:

(2) 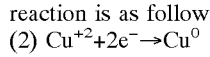

Figure 1:
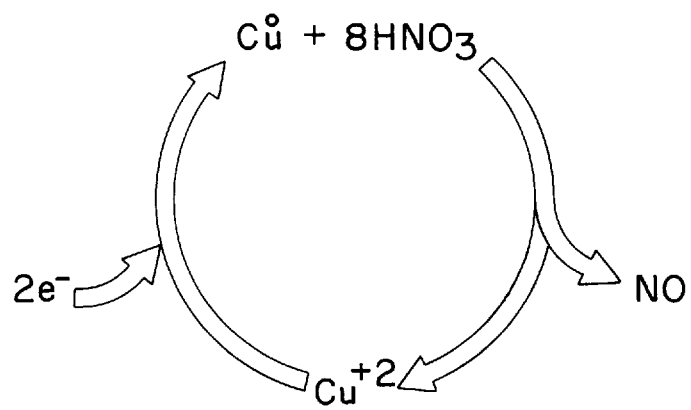
FIG. 1 is a diagram depicting the mechanism of NO generation employed in the present invention.

Thus, the metallic copper will be formed at the surface of a working electrode and will spontaneously undergo a reaction with the nitric acid to produce NO stoichiometrically. The $Cu^{+2}$ ions, accordingly, serve as an electron shuttle between the working electrode and nitric acid and are constantly recycled in the reaction chamber as represented in FIG. 1.

Figure 2:
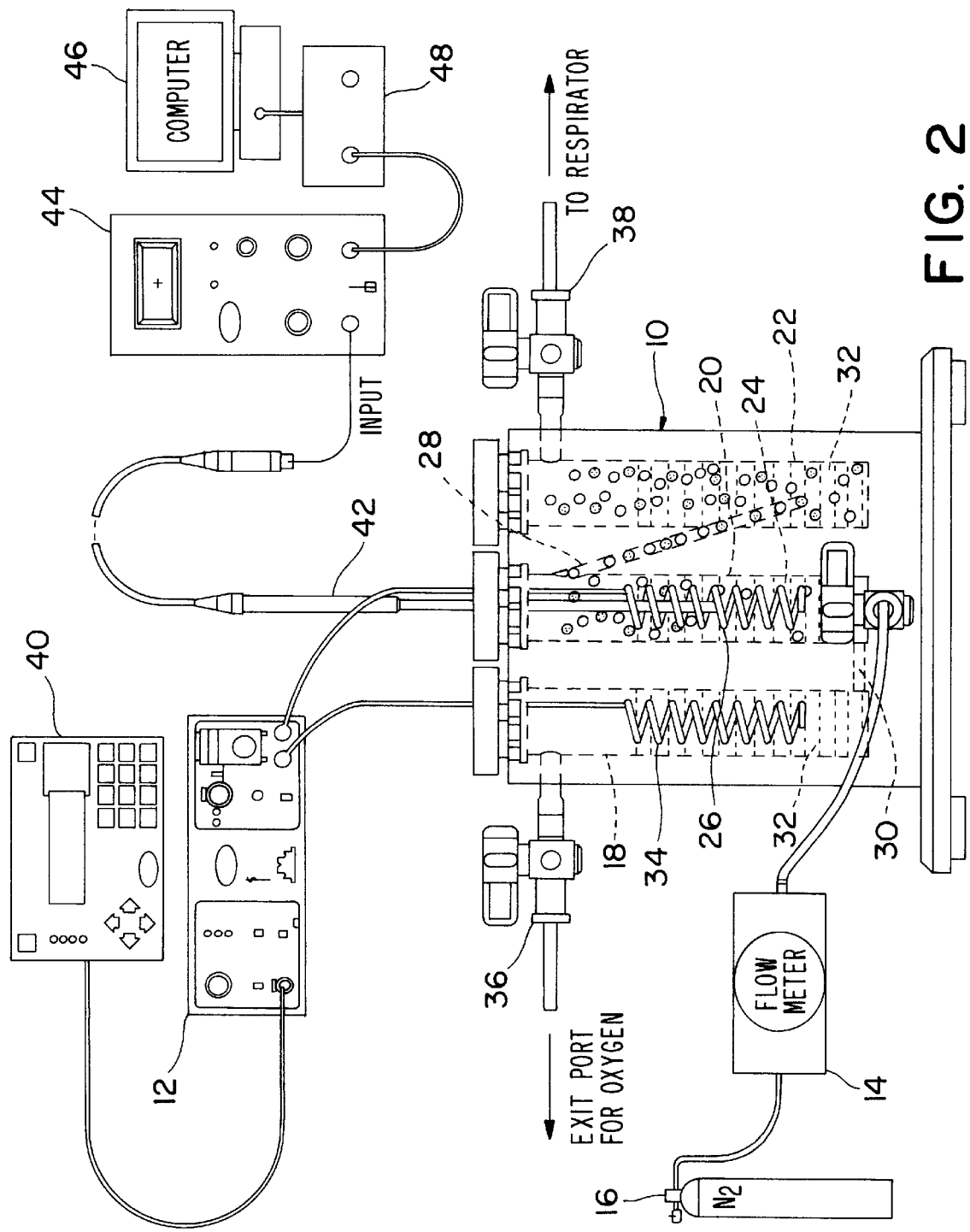
FIG. 2 is a schematic, side-elevational view of a preferred embodiment of apparatus for use in the implementation of the invention.

A NO generator in accordance with the present invention, as shown schematically in FIG. 2, comprises a three-chamber "reaction block", i.e., a housing indicated generally at 10, a constant current source 12, a differential pressure flow meter 14 and a supply of an inert gas 16. The housing or reaction block 10 is comprised of a suitable non-conductive material and includes the three "cells" which define the chambers. The three cells, indicated respectively at 18, 20 and 22, are fluidically connected in series. The intermediately located reaction chamber defining cell 20 contains a solution of 8M nitric acid and 0.1M $Cu^{+2}$, i.e., $CuSO_4$, the solution being indicated at 24. The primary or working electrode 26, i.e., the electrode on which the elemental copper is plated, is immersed in solution 24. Electrode 26, in the embodiment being described, is comprised of platinum. Gas generated in cell 20 is delivered, via a connecting conduit 28, to cell 22.

Cells 18 and 22 contain a buffer solution 32 which, in the disclosed embodiment, is a phosphate buffer. The auxiliary electrode 34, which completes the electrical circuit for the reaction, is immersed in the buffer solution in cell 18. In the disclosed embodiment, the electrode 34 was also composed of platinum. Cell 18 also includes a valved gas discharge port 36 through which the oxygen produced during operation of the NO generator may be vented. Cell 22 also contains a valved gas discharge port 38 through which the generated NO gas may be delivered to a respirator or the like. A glass frit 30 functions to prevent the intermixing of the solutions in cells 18 and 20, and to minimize migration of generated NO to chamber 18, while allowing ion diffusion.

The carrier gas from supply 16, $N_2$ in the example being described, is controllably delivered, via flow meter 14, to the bottom of cell 20. This carrier gas passes through the solution in cell 20 and entrains the generated NO. The carrier gas with the entrained NO then passes, via conduit 28, into cell 22 at a level below the surface of the buffer solution 32. The buffer solution thus serves as a trap for any nitric acid vapor that might be present in the nitric oxide/nitrogen mixture after the carrier gas has passed through the acid-copper sulfate solution 24 in cell 20. The flow meter 14 may be electronically controlled, by means not shown in the drawing, to allow adjustment of the flow rate of the inert carrier gas and thereby provide a measure of control over the concentration of NO in the gas mixture delivered through the discharge port 38. Primary control over the NO concentration in the gas discharged from the NO generator of the present invention is achieved by means of the constant current source 12. The current flow between working electrode 26 and auxiliary electrode 34 will be commensurate with a predetermined rate of NO generation and thus constant current source 12 may be calibrated in terms of NO concentration.

In FIG. 2, for purposes of testing and initial calibration, the NO generator is shown as including a timer 40 for controlling current source 12 and an ISO-NO probe 42. Probe 42 which may, for example, be a Clark-type amperometric NO analyzer which measures REDOX current. Probe 42 will not ordinarily be part of an NO generator manufactured in accordance with the invention. Probe 42 provides an electrical signal having a magnitude commensurate with NO concentration to an ISONO meter 44 both probe 42 and meter 44 are commercial devices available from World Precision Instruments, Inc. of Sarasota Fla. The NO concentration measurements provided by meter 44 are delivered to a computer 46 via an interface 48. The current supplied to the NO generator from source 12 will also be provided as input data to computer 46.

In the practice of the embodiment of the present invention being described, chambers or cells 18 and 22 are filled with a phosphate buffer solution at pH=7.4. Chamber or cell 20 is filled with 8M nitric acid and 0.1M $CuSO_4$. In practice, the composition of the solution in chamber 18 is not critical to operation so long as some ions are present to provide electrical conductivity. The connection of the opposite polarity terminals of constant current source 12 to electrodes 26 and 34 will result in electrolysis of the solutions in chambers 18 and 20. This electrolysis will result in the production of oxygen in chamber 18 and the deposition of metallic copper on the surface of working electrode 26 in chamber 20. The oxygen is vented from chamber 18 via the valved discharge port 36. The metallic copper plated on electrode 26 instantaneously undergoes further reaction with excess 8M nitric acid, i.e., the reaction of Equation (1) occurs. The reaction chamber 20 is purged with the inert carrier gas at a specific flow rate controlled by flow meter 14. The inert carrier gas entrains the NO and carries it into chamber 22. Any traces of nitric acid vapor in the gas mixture exiting reaction chamber 20 will be removed during passage of the gas mixture through the buffer solution 32 in chamber 22.

At least the chambers 18 and 20 are preferably in the form of a disposable cartridge with built-in electrodes. The use of such a replaceable cartridge is in the interest of safety, i.e., the user will not have to handle the concentrated nitric acid.

The above-described coulometric technique allows precise measurement of the amount of metallic copper generated in the presence of nitric acid. As noted above, the $Cu^{+2}$ ions are reduced to metallic Cu in the mixture of 8M nitric acid and spontaneously react with the acid to produce NO and to regenerate the $Cu^{+2}$ ions. Thus, the cycle of $Cu^{+2} \rightarrow Cu^0 \rightarrow Cu^{+2}$ is closed and continuous. The reduction of $Cu^{+2}$ into metallic Cu proceeds without any interference from other electroactive species present in the solution. In a mixture of nitric acid and copper (II) sulphate, the following ions are present:

$H^+$,
$Cu^{+2}$,
$NO^{-2}$,
$NO^{-3}$,
$SO_4^{-2}$,
$OH^-$

The only species that may react upon exposure to a cathodic current are the cations present. However, as may be seen by comparison of the reduction potential of copper and hydrogen ions, the tendency for the reduction of $Cu^{+2}$ ions is greater than that of hydrogen ions. Therefore, $Cu^{+2}$ ions preferentially undergo a cathodic reduction prior to the reduction of any hydrogen ions in the solution.

Proper operation of the present invention may also be attributed to the fact that the reducing power of NO is not strong enough to convert $Cu^{+2}$ ions to $Cu^+$. Accordingly, generated NO exits the acid-copper solution as soon as it is produced and without further chemical interaction with the other species present in the system, i.e., generated NO is not consumed in the reaction cell and thus the process of NO generation is quantitative.

Figure 3:
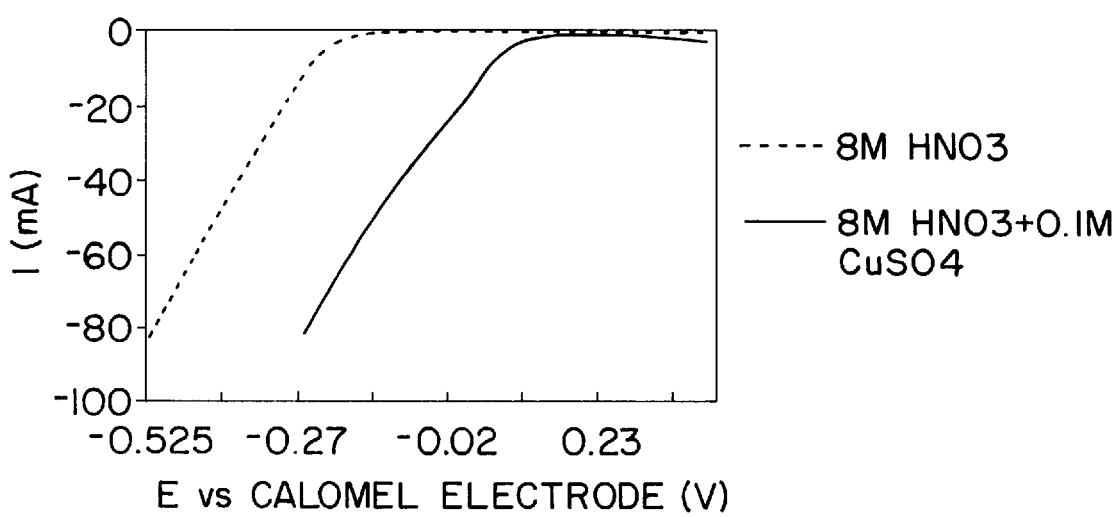
FIG. 3 shows current-voltage curves for the precursor (0.10M $Cu^{+2}$) and the supporting electrolyte (8M nitric acid)

Constant-current coulometry, i.e., the mode of operation of the present invention, is based upon Farraday's law. In accordance with Farraday's law, the quantity of electrical charge passed through a cell is directly proportional to the number of equivalents of the reduced copper at the surface of an electrode. In order to take advantage of Farraday's law in a quantitative manner, the reaction at the working electrode must be limited to the chemical species of interest to assure that the charge consumed by the desired electron transfer reaction is essentially equal to the charge applied to the cell. In practice, difficulties may arise due to the presence of other "current sinks" within the system such as electrolysis of electroactive species in the solution at a rate controlled by diffusion to the electrode, absorption of the electroactive species on the surface of the electrode, oxidation or reduction of chemical impurities in the electrolyte and the charging of the double-layer capacitance at the surface of the electrode. The total amount of charge represented by such "current sinks" can be considered as a single source and be designated as "residual current". The "residual current" is a function of electrode potential. Accordingly, knowledge of the current-voltage curves for the precursor and the supporting electrolyte will provide information for determining the applied current at which the maximum current efficiency can be achieved. FIG. 3 depicts a current vs. applied voltage plot for a pure solution of 8M nitric acid as well as for a mixture of 8M nitric acid and 0.1M copper (II) sulfate. In collecting the data presented in FIG. 3, the electrode potential was scanned from 400 mV down to −525 mV vs. a calomel electrode at a scan rate of 100 mV/s. FIG. 3 proves that the reduction Of $Cu^{+2}$ happens prior to the reduction of $H^+$ions because the cathodic current increases rapidly at lower potentials when $Cu^{+2}$ is present in the solution. FIG. 3 also shows that the potential at which the maximum current efficiency is achieved can be determined by measuring the residual current, i.e., current efficiency can be calculated as follows:

(3) % Current Efficiency=100 $(I_{applied}-I_{residual})/I_{applied})$

Figure 4:
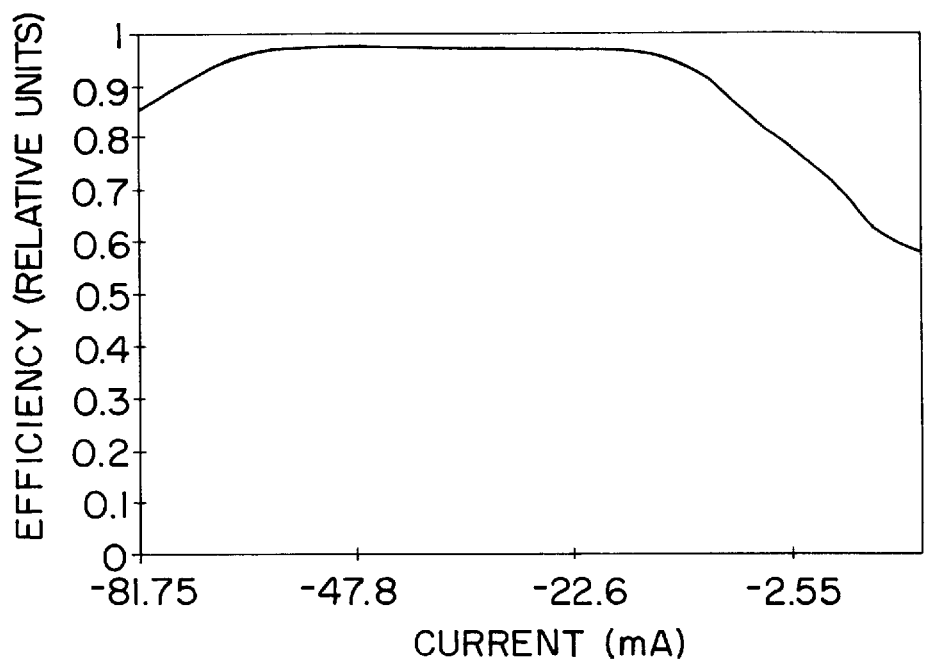
FIG. 4 is a graphical representation of the efficiency of an NO generator in accordance with the present invention as a function of current.

The quantum efficiency curve of FIG. 4, calculated using equation (1) above for all of the data shown on FIG. 3, indicates that maximum current efficiency with a particular set of platinum electrodes was achieved with a current maintained within the range of −10 to −60 mA, peak efficiency being at −50 mA. The current efficiency of the system of this optimal current can be calculated as follows:

Potential of the electrode −120 mV
$I_{applied}$=−50.0 mA
$I_{residual}$=−1.25 mA
% Current Efficiency=100 (50−1.25)/50=97.50

Figure 5:
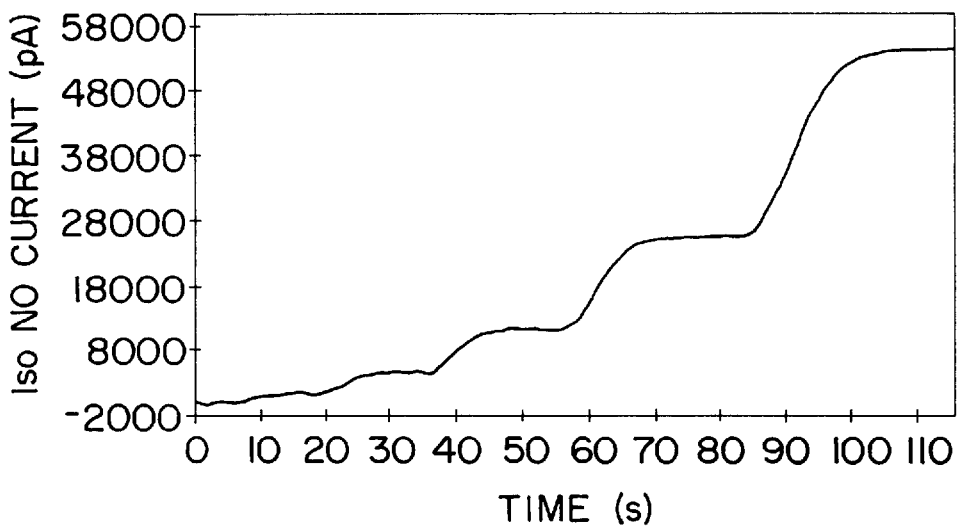
FIG. 5 graphically depicts the relationship between NO concentration and time during calibration of an NO generator in accordance with the invention.
Figure 6:
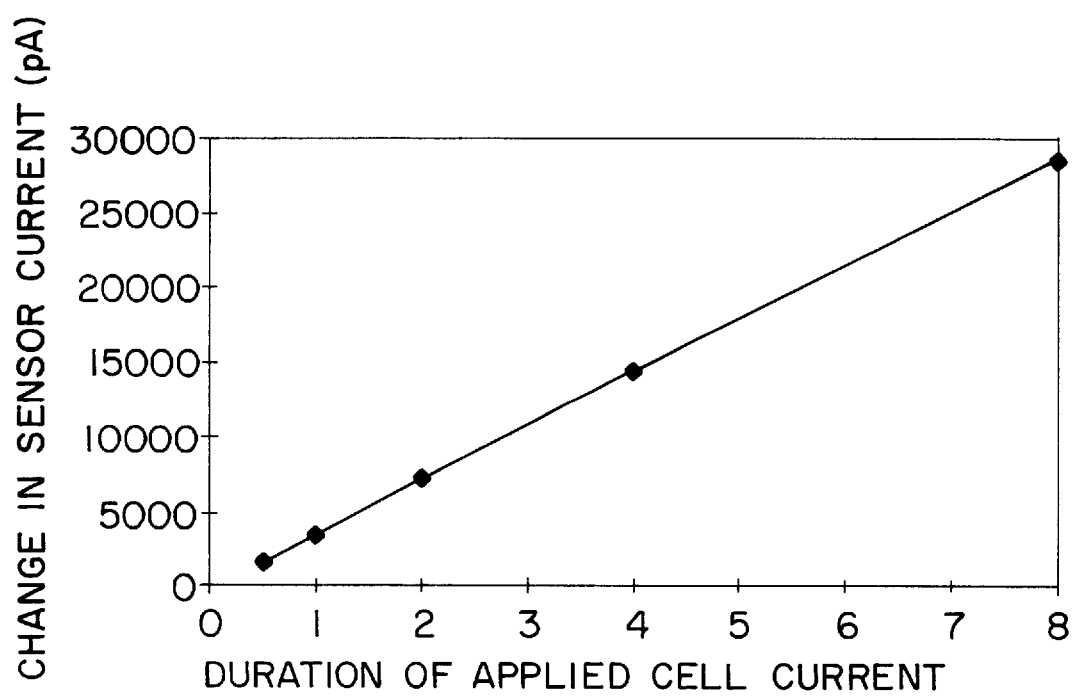
FIG. 6 is a calibration curve showing the change in current of an NO analyzer as a function of time.

Data from an actual test on apparatus as shown in FIG. 2, such apparatus employing a pair of platinum electrodes ten (10) cm in length and one (1) mm in diameter, is presented in FIG. 5. FIG. 5 graphically depicts the relationship between the current of the NO analyzer 42, 44, which is proportional to NO concentration, and time during a calibration experiment. In collecting this data, the constant current source 12 was set to supply an optimal constant current of 50 mA. The timer 40 was used to switch the current source on and off in order to supply a specific quantity of charge to the system. In obtaining the test results, current source 12 was turned on and off for 0.5, 1, 2, 4 and 8 seconds with a pause between cycles. The current output of the NO probe 42 was monitored continuously to measure the level of generated NO for a given amount of charge supplied. A calibration curve, based upon data obtained from FIG. 5, is shown in FIG. 6. In FIG. 6, time is proportional to the charge passed through the system because constant current was supplied. FIG. 6 thus shows the change in the current of the NO analyzer, which as noted is proportional to NO concentration, as a function of the period of time the current is applied. The test results show that the generated NO concentration is a linear function of the total amount of charge transferred into the reaction cell 20 and that the response time of the NO generator of the present invention is within a few seconds for the generation of a particular NO concentration. However, although nitrate ions are spontaneously reduced to NO gas in a fraction of a second, there is a time lag of a few minutes when the NO generator of the invention is started before a standard supply of NO is provided at the discharge port 38. This time delay is due to the saturation and equilibrium of NO in the solutions present in chambers 20 and 22. After equilibrium is obtained, however, any change in the supply of electrical current translates into corresponding NO concentration changes within seconds. Removal of NO from the acid-copper mixture is facilitated because of the solubility of NO in the liquid phase.

FIG. 5 also shows the response time of an NO generator in accordance with the invention at different levels of current supplied to the apparatus. The response time is a combination of two different factors. The first of these factors is the rate of chemical conversion of nitrate ions, in the nitric acid, to NO in the presence of metallic copper. The second factor is related to the response time of the NO probe 42 which is about 10–12 seconds. Since the chemical conversion of nitrate to NO is relatively faster in respect to the response time of the probe, the data provided in FIG. 5 reflects the response time of the probe rather than the conversion rate.

The only consumable reagent in the above-described NO generator is nitric acid. Over time nitrate ions are converted to NO and the concentration of the nitric acid decreases below the critical concentration (8M) at which metallic copper can react with nitric acid to generate NO. However, only a small quantity of NO is generated at any time because NO is diluted with nitrogen or another inert gas to produce a standard supply of gas having NO measured in parts per million. Accordingly, the reagent will last for a long period of time before being exhausted. For example, 30 ml of 8.5M nitric acid will produce 336 ml of pure NO at standard conditions (STP) before the concentration of the nitric acid falls to 8M. In practice, 336 ml NO can produce approximately 17,000,000 ml of therapeutic gas mixture ($NO+N_2$) of 20 ppm. This amount of NO, i.e., 336 ml. would thus be sufficient to generate a standard supply of NO gas, 20 ppm, for over six hours at a flow rate of 500 ml/min.

While a preferred embodiment has been shown and described, various modifications and substitutions may be made thereto without departing from the spirit and scope of the invention. Accordingly, it is to be understood that the present invention has been described by way of illustration and not limitation.

What is claimed is:

1. A method for controllably generating a gas mixture which includes a preselected quantity of nitric oxide comprising the steps of:

disposing a first electrode in a closed first cell which contains a solution of nitric acid and a source of copper ions;

disposing a second electrode in a second cell which contains an electrolyte;

controllably establishing a flow of electric current between said electrodes to electroplate elemental copper from said solution onto said first electrode at a rate commensurate with the magnitude of the current, the elemental copper reacting with the nitric acid to generate nitric oxide gas;

establishing a flow of carrier gas through said solution in said first cell to provide a gas mixture comprising the generated nitric oxide gas entrained by said carrier gas;

extracting said gas mixture from said first cell;

cleaning said extracted gas mixture to remove nitric acid vapor therefrom; and discharging the cleansed gas mixture.

2. The method of claim 1 wherein the nitric oxide in the gas mixture has a concentration which is controlled by varying the established current flow between said electrodes and varying the established flow of the carrier gas.

3. The method of claim 2 further comprising the step of venting gas generated in said second cell.

4. The method of claim 2 wherein said step of establishing current flow between said electrodes includes creating a path for ion diffusion between said first and second cells.

5. The method of claim 4 wherein said ion diffusion path isolates said electrolyte in said second cell from said solution in said first cell and wherein the step of controlling current flow between said electrodes further comprises:

connecting opposite polarity terminals of a source of direct current to respective of said electrodes.

6. The method of claim 5 wherein said step of cleansing comprises:

causing the extracted gas mixture to flow through a buffer solution.

7. The method of claim 6 further comprising the step of venting gas generated in said second cell.

8. The method of claim 1 wherein said step of establishing current flow between said electrodes includes creating a path for ion diffusion between said first and second cells.

9. The method of claim 8 wherein said ion diffusion path isolates said electrolyte in said second cell from said solution in said first cell and wherein the step of controlling current flow between said electrodes further comprises:

connecting opposite polarity terminals of a source of direct current to respective of said electrodes.

10. The method of claim 1 wherein said step of cleaning comprises:

causing the extracted gas mixture to flow through a buffer solution.

* * * * *